United States Patent [19]

Nissen et al.

[11] 4,049,571
[45] Sept. 20, 1977

[54] MANUFACTURE OF A CATALYST COMPOSITION CONTAINING ZINC AND NICKEL OR COBALT

[75] Inventors: Axel Nissen, Leimen; Werner Fliege, Otterstadt; Dieter Voges, Mannhein, all of Germany

[73] Assignee: BASF Aktiengesellschaft, Ludwigshafen (Rhine), Germany

[21] Appl. No.: 688,763

[22] Filed: May 21, 1976

[30] Foreign Application Priority Data

June 7, 1975 Germany .......................... 2525506

[51] Int. Cl.² .................. B01J 31/04; B01J 23/80
[52] U.S. Cl. .................... 252/430; 252/473; 260/593 R
[58] Field of Search ................... 252/430, 473

[56] References Cited

U.S. PATENT DOCUMENTS

| 2,666,756 | 1/1954 | Boyd et al. ............... 252/473 X |
| 3,522,024 | 7/1970 | Billings et al. ........... 252/430 X |
| 3,781,350 | 12/1973 | Fujita et al. ............. 252/473 X |
| 3,853,922 | 12/1974 | Yamaguchi et al. ......... 252/473 X |

*Primary Examiner*—Patrick P. Garvin
*Attorney, Agent, or Firm*—Keil, Thompson & Shurtleff

[57] ABSTRACT

A process for the manufacture of a catalyst capable of causing condensation of aldehydes with ketones or ketones with each other while simultaneously hydrogenating the resulting olefinically unsaturated ketones to saturated ketones in the presence of hydrogen without attacking the ketone group, and containing zinc in addition to nickel or cobalt. The catalyst is subjected, prior to use, to a surface after-treatment with a zinc salt.

8 Claims, No Drawings

MANUFACTURE OF A CATALYST COMPOSITION CONTAINING ZINC AND NICKEL OR COBALT

The synthesis of higher saturated ketones in a single operation from aldehydes and ketones or ketones and ketones (e.g. 2-methyloctanone-2 from butanal and methyl isopropyl ketone according to the following equation (1))

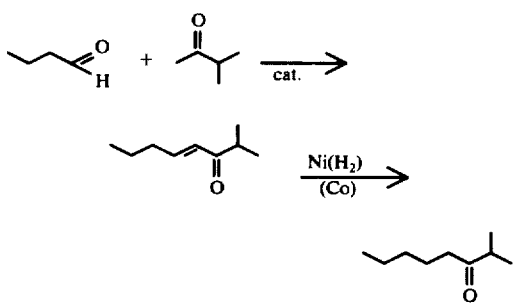

is generally effected using a supported catalyst containing zinc oxide as aldol ingredient and nickel (or cobalt and copper) as hydrogenation ingredient.

It is of no significance whether the aldol (zinc) ingredient and the hydrogenating (nickel) ingredient are disposed on separate or the same catalyst particles. Where they are disposed on separate catalyst particles, the resulting catalyst is referred to below as a "mixed" catalyst.

The reaction has hitherto been carried out in a single step in the gas phase, although a longer catalyst life may be achieved when the reaction is carried out in liquid phase rather than in the gas phase. However, it is difficult to effect hydrogenation of the double bond of the intermediate α,β-unsaturated ketone in the liquid phase without attacking the carbonyl groups also contained in the reaction medium, i.e. both the carbonyl groups of the α,β-unsaturated ketone and those of the aldehyde and ketone used as starting materials.

According to F. Zymalkowski "Katalytische Hydrierung" (F. Enke Verlag, Stuttgart, 1965, page 84), zinc ions, when added to metals of group VIII of the Periodic Table (so-called transition metals), effect hydrogenation of the carbonyl group whilst preserving the double bond. This would mean that it is possible to poison catalysts of group VIII by zinc additives in such a manner that, for example, only the carbon-carbon triple bond but not the carbon-carbon double bond is hydrogenated (German Laid-Open Specification No. 2,156,144 and Published Application DAS No. 1,115,238).

The effect that hydrogenation catalysts of Group VIII preferentially hydrogenate the carbonyl group but not the double bond in the presence of divalent zinc (e.g. zinc oxide) appears to play only a minor role in gas phase reactions, since the prior art hydrogenations of α,β-unsaturated ketones and direct processes of the above kind are preferably carried out in the gas phase when their catalyst system contains a metal of group VIII and zinc oxide. In this context reference is made to Japanese Patent Publication No. 72 15 180, U.K. Pat. No. 1,328,143 (where a mixture of saturated ketone and saturated alcohol is obtained) and German Laid-Open Specification No. 2,023,512.

In the industrially advantageous liquid-phase process the presence of zinc oxide effects, at a temperature of 180° to 220° C as required for the reaction, extensive hydrogenation of the carbonyl groups contained in the reaction medium, so that the main product consists of the alcohols corresponding to the aldehydes and ketones used, small amounts of the alcohol corresponding to the ketone required and, in many cases, no desired product.

It is an object of the invention to provide a catalyst composition for the manufacture of ketones obtainable by aldol condensation of low molecular weight aldehydes or ketones with low molecular weight ketones and hydrogenation of the intermediate α,β-unsaturated ketones formed at a temperature above about 150° C in the liquid phase, which catalyst composition contains essentially nickel and/or cobalt and zinc oxide and a chemically inert support.

It is another object of the invention to provide a process for the manufacture of a catalyst composition containing zinc and nickel or cobalt intended to achieve higher selectivity in the hydrogenation of α,β-unsaturated ketones to the corresponding saturated ketones, wherein the catalyst is partially deactivated (partially poisoned) by a special treatment.

We have found that such a catalyst composition is obtained if a catalyst composition containing nickel or cobalt or compounds thereof and zinc oxide is post-treated with a zinc salt of a carboxylic acid. The said post-treatment may be carried out on the unreduced composition containing nickel or cobalt in the form of compounds or preferably on the reduced composition containing metallic cobalt or nickel. The catalyst composition may contain a chemically inert support.

A catalyst composition thus treated (passivated) provides the saturated ketone as the main reaction product (e.g. 2-methyloctanone-3 from butanal and methyl isopropyl ketone) with almost complete conversion of the starting materials.

To this end, the catalyst composition is treated, advantageously after being placed in the reactor, with a solution or suspension of a zinc salt of a carboxylic acid, preferably a low molecular weight straight-chain or branched-chain aliphatic or aromatic carboxylic acid (e.g. zinc acetate or zinc 2-ethyl hexanate or, if desired, zinc benzoate or similar compounds). The carboxylic acid generally contains from 2 to 20 carbon atoms. Appropriate solutions or suspensions of the zinc salts may contain the salt in almost any practicable concentrations. For example, solution or suspension concentrations from 0.1 to 50% are suitable.

Advantageously, the solvent or dispersing agent for the zinc salt consists of the appropriate reaction mixture of aldehyde and ketone. If zinc acetate is used, this should be in solution, since crystals of this salt may damage the pumps. The addition of up to 10% of water and from 2 to 5% of the carboxylic acid corresponding to the aldehyde may facilitate solution. Zinc salts of organic acids which are sparingly soluble in the reaction mixture but consist of crystals which are soft enough to be conveyed by the pumps without damage thereto may be used in the form of suspensions.

The catalyst is treated with such a solution or suspension for several hours or days, for example for 72 hours. This may be effected, for example, by pump-circulating the said solution or suspension to the composition at a temperature of from about 50° to 160° C. The most suitable minimum time and temperature of the treatment is advantageously determined by a simple experiment. As a general guide, a treatment time of from about 10 to 200 hours may be stated, the longer periods being generally uncritical and subject to economical factors.

Following this treatment, the temperature is raised to from 180° to 220° C, i.e. the reaction temperature, and the feed of starting materials is commenced. When the reaction mixture is also used as solvent, there is no need for a rinsing operation.

The best results are obtained when from about 0.01 to 20% of a zinc salt of a higher aliphatic carboxylic acid having from about 11 to 20 carbon atoms, e.g. zinc stearate or zinc palmitate, are added to the solution of the zinc salt of a short-chain aliphatic carboxylic acid containing up to 10 carbon atoms (e.g. zinc acetate). These salts are generally sparingly soluble in aldehydes or ketones but their crystal particles are so small and soft that a suspension thereof may be pumped by conventional piston pumps without damage thereto.

The use of such a mixture of zinc salts reduces the treatment time from, say, 72 to 48 hours as compared with the use of acetate alone. In addition, the degree of poisoning of the supported catalyst shows better reproducibility and this is desirable for improved control of the reaction. Clearly there is a very fine deposit of sparingly soluble salts on the catalyst or catalyst composition, which salts are not dissolved or washed away from the catalyst in a short period.

The following specific remarks relate to the manufacture of the catalyst compositions of the invention:

Nickel or cobalt and, if desired, copper or other conventional doping ingredients are mixed, separately or together, with zinc in conventional manner to form a catalyst composition. In general, a support which is essentially chemically inert, for example γ-aluminum oxide or some other inert support, is treated with the catalytically active metals or salts thereof whilst in a suitable form (pellets, spheres, grains) or the said metals or salts thereof are precipitated, kneaded or otherwise combined with a support precursor. After suitable pretreatment (heating, tempering, reduction in, say, a stream of hydrogen), the catalyst composition is treated in the manner proposed in the present invention. Suitable catalyst compositions have contents of, say, nickel or cobalt of from 3 to 50%. The support is advantageously of aluminum oxide, a titanium dioxide or zirconium dioxide. Silicic acid, pumice and other silicates have as yet been less satisfactory. A further suitable (metal component is, in particular, copper. This is generally used only in minor quantities (e.g. from 1 to 2%, based on the weight of the total composition).

The content of zinc on a suitable support as described above may be from 1 to 10%. However, since zinc oxide is not attacked in the reduction of nickel, it may be used without a support provided it is part of a mixed catalyst. The use of unsupported nickel or cobalt catalysts is also possible in principle, but apparently to no particular advantage; it is therefore not generally usual for economical reasons.

The process for the manufacture of the catalyst has a surprising result since the prior art indicates that the further reduction of the ketone to the alcohol is due to the presence of zinc; "passivation" was not to be expected.

The reaction conditions suitable for efficient operation of the novel catalyst composition are generally not different from those selected for the prior art catalysts. For example, the reaction mixture is hydrogenated at from 150° to near 250° C at a hydrogen pressure of from 20 to 80 bars. Solvents are not generally necessary if the pressure is high enough. However, the presence of solvents, even minor quantities of water, generally has no influence on the progress of the reaction.

The process for the manufacture of the catalyst is related to the manufacture of unsaturated as well as saturated ketones.

It is therefore a further object of the invention to provide an advantageous process for the manufacture of ketones. In general, these ketones are known.

For example, the invention may be advantageously used to obtain ketones of the general formula

$$R^1-CO-R^2$$

in which $R^1$ and/or $R^2$ denote straight-chain or branched-chain alkyl, cycloalkyl, aryl or aralkyl, the total number of carbon atoms in $R^1$ and $R^2$ being at least 4. In general, at least one radical contains at least 3 carbon atoms. In general, ketones having a total of more than 20 carbon atoms including the keto group are industrially less interesting, although their synthesis is possible according to the present invention.

Thus the starting materials for such ketones are generally aldehydes of, say, from 2 to 17 carbon atoms or ketones of, say, from 3 to 17 carbon atoms as one component, whilst the other component is, for example, a ketone of from 3 to 17 carbon atoms. Usually, the starting ketone has a keto group in the 2-position, i.e. it possesses an isolated methyl group following the keto group. Thus suitable aldehydes are acetaldehyde, propionaldehyde, n-butyraldehyde, isobutyraldehyde, pentanal-1,2-methylbutanal, 2-methylpentanal and benzaldehyde, for example.

Examples of suitable ketones are, accordingly, acetone, methyl ethyl ketone, methyl isopropyl ketone, 4-methylheptanone-2, acetophenone, and other ketones having the keto group in the 2-position and which are generally saturated or aromatic straight-chain or branched ketones.

The reaction is advantageously carried out in such a manner that the aldehyde to be used is present in a stoichiometrically minor amount if it is desired to obtain a particularly uniform reaction. However, since the resulting mixture of substances is generally easy to separate, the reaction may be carried out in some other manner for, say, economical reasons. If the aldehyde is present in excess, the new ketone formed will usually be converted to a certain extent to a further ketone having a longer chain.

EXAMPLE 1

In this and the following Examples, a 3 1 tubular reactor is used which is filled with catalyst pellets of the composition stated. The diameter of the pellets is 4 mm. During the reaction, the reaction mixture is passed through the reactor at a rate of 1 liter per liter of catalyst per hour, the temperature being maintained at 200° C and the pressure at 30 bars (corresponding to a hydrogen partial pressure of about 5 bars).

The catalyst composition consisting of 2 parts by weight of a catalyst containing 10% of nickel, 10% of cobalt and 4% of copper on aluminum oxide and 1 part by weight of a catalyst containing 20% by weight of zinc oxide on aluminum oxide is reduced in the usual manner. 3 l of a solution having a temperature of 30° C are then placed in the reactor, the solution consisting of 53% by weight of acetone, 32.5% by weight of 2-methylpropanal (containing 1.4% by weight of methylpropionic acid), 8.5% by weight of water and 6% by weight of zinc 2-ethyl hexanate. The liquid is then circulated for 78 hours at a temperature of 160° C under nitrogen.

The temperature is then raised to 200° C and the previous liquid is replaced by a mixture of 62% of acetone and 38% of 2-methylpropanal and the nitrogen is replaced by hydrogen. After an onstream period of 24 hours using this mixture, a sample is analyzed by gas chromatography. For purposes of comparison, the experiment is repeated without the pretreatment of the invention.

The results of this experiment and the comparative test are given in the Table below, where the figures are percentages which do not consider the water content.

TABLE 1

|  | Following pretreatment with 6% of zinc-2-ethylhexanate for 78 hours | no pretreatment |
|---|---|---|
| acetone | 30.1 | 22.4 |
| methylpropanal | 4.6 | 1.8 |
| isopropanol | 0.7 | 36.2 |
| methylpropanol | 10.6 | 32.8 |
| 5-methyl-hexanone-2 | 36.8 | 0.3 |
| 5-methyl-hexanol-2 | 0.1 | 1.4 |
| 5-methyl-hexen-3-one-2 | 8.5 | 0 |

EXAMPLE 2

Following conventional reduction of a catalyst composition containing 16% of nickel and 4% of zinc oxide on aluminum oxide, a solution having a temperature of 50° C and consisting of 30% w/w of acetone, 30.7% w/w of 2-methylpropanal (containing 1.4% w/w of methylpropionic acid), 8.1% w/w of water and 5.6% w/w of zinc 2-ethyl hexanate, in which 5.6% w/w of zinc palmitate is suspended, is placed in the reactor.

In different tests, pretreatments lasting 15, 30 and 45 hours at 100° C under nitrogen are carried out. In each case, following heating to 200° C and replacement of nitrogen by hydrogen, a feed of 62% w/w of acetone and 38% w/w of 2-methylpropanal is commenced. After 24 hours, a sample is analyzed by gas chromatography (Table 2 below neglects the water contained; the figures are again percentages).

TABLE 2

|  | Duration of passivation (in hours) | | |
|---|---|---|---|
|  | 15 | 30 | 45 |
| acetone | 42.6 | 34.0 | 34.9 |
| methylpropanol | 2.0 | 2.7 | 6.7 |
| isopropanol | 10.1 | 5.4 | 1.2 |
| methylpropanol | 24.7 | 16.6 | 4.2 |
| 5-methyl-hexanone-2 | 17.3 | 37.1 | 33.9 |
| 5-methyl-hexanol-2 | 3.5 | 2.3 | 0.6 |
| 5-methyl-hexen-3-one-2 | 0.9 | 1.1 | 5.6 |

EXAMPLE 3

Following conventional reduction of a catalyst consisting of 4 parts by weight of pellets composed of 10% of Ni, 10% of Co, 4% of Cu on Al$_2$O$_3$ and 1 part by weight of pellets consisting of 20% of ZnO on Al$_2$O$_3$, 3 l of a solution having a temperature of 50° C and consisting of 66.7% w/w of methyl isopropyl ketone, 16.7% w/w of butanal, 8.3% w/w of water, 1.7% w/w of butyric acid and 3.3% w/w of zinc acetate in which 3.3% w/w of zinc stearate is suspended, is placed in the reactor, the contents of which are treated with the continuously circulated suspension for 48 hours at 130° C under nitrogen.

After heating to 200° C and replacement of the nitrogen by hydrogen, a feed of 80% w/w of methyl isopropyl ketone and 20% of butanal is commenced. After 24 hours, a sample is analyzed by gas chromatography (the percentages in Table 3 below neglect the water contained):

TABLE 3

| butanal | 1.6 |
|---|---|
| butanol | 1.1 |
| methyl isopropyl ketone | 64.1 |
| 2-methylbutanol-3 | 0.5 |
| 2-methyloctanone-3 | 17.1 |
| 2-methylocten-4-one-3 | 3.5 |
| 2-methyloctanol-3 | 0 |

EXAMPLE 4

Following conventional reduction of a catalyst composed of 8% of Ni, 8% of Co, 4% of ZnO on Al$_2$O$_3$, 3 l of a suspension having a temperature of 25° C and consisting of 7.3% w/w of zinc stearate in 90.9% w/w acetone and 1.8% w/w of 2-methylpropionic acid are placed in the reactor and circulated therethrough for 48 hours under nitrogen at 140° C. The reactor is then heated to 200° C and the nitrogen is replaced by hydrogen and a feed of 65.8% w/w of acetone and 34.2% w/w of benzaldehyde is continuously passed therethrough at the rate given in Example 1. After 24 hours, a sample is analyzed by gas chromatography (Table 4; figures and percentages):

TABLE 4

| acetone | 47.5 |
|---|---|
| benzaldehyde | 1.4 |
| isopropanol | 0.6 |
| benzyl alcohol | 3.2 |
| 4-phenylbutanone-2 | 26.4 |
| 4-phenylbutanol-2 | 0 |
| 4-phenylbuten-3-one-2 | 3.8 |

EXAMPLE 5

The reactor is filled with a catalyst composition containing 10% of nickel oxide, 10% of cobalt oxide and 4% of zinc oxide on Al$_2$O$_3$.

Prior to the reducing treatment, the catalyst composition is treated for 48 hours at 180° C with 3 l of a suspension of 7.3% of zinc stearate in a mixture of 63.0% w/w of acetone, 27.9% w/w of 2-ethylhexanol and 1.8% w/w of 2-methylpropionic acid. Following removal of the solution and drying with nitrogen, the composition is reduced in the usual manner. Following this preparation, a mixture of 69.3% by weight of acetone and 30.7% by weight of 2-ethylhexanol is continuously reacted at 200° C.

A sample taken after 24 hours is analyzed by gas chromatography to give the following results:

TABLE 5

| | |
|---|---|
| acetone | 50.6 |
| 2-ethylhexanol | 3.4 |
| isopropanol | 0.9 |
| 5-ethylnonanone-2 | 20.7 |
| 5-ethylnonanol-2 | 0.3 |
| 5-ethylnonan-3-one-2 | 2.6 |

We claim:

1. An improved process for the manufacture of a catalyst essentially containing nickel and/or cobalt and zinc oxide and suitable for the synthesis of ketones by aldol condensation of low molecular weight aldehydes or ketones with low molecular weight ketones and hydrogenation of the intermediate α, β-unsaturated ketones formed at a temperature above about 150° C in the liquid phase, which process comprises treating a catalyst composition containing a catalytically active amount of zinc oxide and a catalytically active amount of at least one of nickel and cobalt or at least one of a hydrogen-reducible compound of nickel or cobalt at about 50° to 160° C with a solution or suspension at a concentration of 0.1 to 50% of at least one zinc salt of an aliphatic or aromatic hydrocarbyl carboxylic acid having 2 to 20 carbon atoms.

2. A process as claimed in claim 1, wherein the catalyst composition contains a chemically inert support for the catalytically active components.

3. A process as claimed in claim 1, wherein the treatment is effected with a solution of a dissolved zinc salt of an aliphatic carboxylic acid having less than 10 carbon atoms in the molecule and/or a suspension of a zinc salt of an aliphatic carboxylic acid having more than 10 carbon atoms in the molecule.

4. A process as claimed in claim 1, wherein the zinc salt used is zinc acetate.

5. A process as claimed in claim 1, wherein the zinc salt used is zinc stearate.

6. A process as claimed in claim 1 wherein said catalyst composition consists essentially of a catalytic amount of nickel and/or cobalt or nickel oxide and/or cobalt oxide on a chemically inert support plus zinc oxide on a chemically inert support, said composition being in the form of shaped particles suitable for use as a catalyst.

7. A process as claimed in claim 1 wherein the catalyst composition is treated with said zinc salt for about 10 to 200 hours.

8. A process as claimed in claim 1 wherein said catalyst composition consists essentially of nickel and/or cobalt at a concentration of 3 to 50% on a chemically inert support, an optional minor quantity of copper on said support and zinc oxide in an amount of 1 to 20% on a catalyst support.

* * * * *